United States Patent
Samari

(10) Patent No.: US 8,687,226 B2
(45) Date of Patent: *Apr. 1, 2014

(54) MEDICAL DATA RECORDING SYSTEM

(75) Inventor: Cyrus Kurosh Samari, Burnsville, MN (US)

(73) Assignee: Sorna Corporation, Eagan, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/287,892

(22) Filed: Nov. 2, 2011

(65) Prior Publication Data

US 2012/0116808 A1 May 10, 2012

Related U.S. Application Data

(63) Continuation of application No. 12/265,331, filed on Nov. 5, 2008, now Pat. No. 8,059,304, which is a continuation of application No. 09/753,792, filed on Jan. 3, 2001, now Pat. No. 7,965,408.

(60) Provisional application No. 60/205,751, filed on May 19, 2000.

(51) Int. Cl.
*G06K 15/00* (2006.01)
*G06F 3/12* (2006.01)

(52) U.S. Cl.
USPC .................. 358/1.18; 358/1.1; 358/1.15

(58) Field of Classification Search
None
See application file for complete search history.

(56) References Cited

U.S. PATENT DOCUMENTS

| | | | |
|---|---|---|---|
| 5,272,625 A | 12/1993 | Nishihara | |
| 5,518,325 A | 5/1996 | Kahle | |
| 5,542,768 A | 8/1996 | Rother | |
| 5,717,841 A * | 2/1998 | Farrell et al. | 358/1.15 |
| 5,721,891 A | 2/1998 | Murray et al. | |
| 5,724,582 A | 3/1998 | Pelanek et al. | |
| 5,914,918 A | 6/1999 | Lee | |
| 6,041,703 A | 3/2000 | Salisbury | |
| 6,115,486 A | 9/2000 | Cantoni | |
| 6,260,021 B1 | 7/2001 | Wong | |
| 6,366,966 B1 | 4/2002 | Laney et al. | |
| 6,574,629 B1 | 6/2003 | Cooke, Jr. et al. | |
| 6,760,755 B1 | 7/2004 | Brackett | |

(Continued)

OTHER PUBLICATIONS

Huang, H.K.m D.Sc. "PACS Basic Principles and Applications," wiley-Liss, Inc. 1999, Title page, Copyright Notice page, Table of Contents, Chapter 7, Sections 10.5 and 12.5 (45 Pages).

(Continued)

*Primary Examiner* — Dov Popovici
(74) *Attorney, Agent, or Firm* — Billion & Armitage; Richard E. Billion

(57) ABSTRACT

A device for recording information on CDRs or other recording media and printing file information for observing what is recorded thereon. The information may be medical images such as x-rays, cat scans, magnetic resonance images, or sonograms. The discs can have patient names and other information selected from information stored thereon, printed on the disc as well as logos for the hospital, service provider or trademarks. The discs can be automatically loaded into the recorder and printer. The fields of information or logos printed on the discs can be changed to suit the user. A database creates and updates a directory of patient files so the discs can be located and the images thereon viewed for each patient. The discs have software allowing the computer to view the images on the disc so that a personal computer not having imaging software can operate the disc.

42 Claims, 4 Drawing Sheets

(56) References Cited

U.S. PATENT DOCUMENTS

| | | | |
|---|---|---|---|
| 6,988,074 | B2 | 1/2006 | Koritzinsky et al. |
| 7,302,164 | B2 * | 11/2007 | Wright et al. ............ 386/225 |
| 8,059,304 | B2 * | 11/2011 | Samari ................. 358/1.18 |
| 2007/0050216 | A1 | 3/2007 | Wright et al. |
| 2013/0021635 | A1 * | 1/2013 | Wright et al. ............ 358/1.13 |

OTHER PUBLICATIONS

Mehta, A. et al., "Enhancing Availability of the Electronic Image Record for Patients and Caregivers During Follow-Up Care," Journal of Digital Imaging, vol. 12, No. 2, Supp.1, May 1999, pp. 78-80 (3 Pages).

MEDIMAGE ACOM.Convert DICOM Archiving & Viewing Station Software Vers. 4.42 User Manual, Sep. 5, 1999 (66 Pages).

Cedar Technologies—CD-R Publishers—sales literature, Jan. 3, 2001.

Sencor—Internet site—sales literature, Jan. 3, 2001 (copyright 1994-2001).

Dicom Cube—Internet site—sales literature, Jan. 2, 2001 (copyright 1999).

Algotec—Internet site—sales literature, Jan. 2, 2001.

TDK Medical—Internet site—sales literature, Jan. 3, 2001.

* cited by examiner

MEDICAL DATA RECORDING SYSTEM

RELATED APPLICATIONS

This application is a Continuation Application of U.S. application Ser. No. 12/265,331, filed 5 Nov. 2008, now U.S. Pat. No. 8,059,304 entitled "Medical Data Recording System", which in turn is a Continuation Application of U.S. application Ser. No. 09/753,792 (now U.S. Pat. No. 7,965,408), filed 3 Jan. 2001, entitled "Medical Data Recording System", which claims the benefit of U.S. Provisional Application No. 60/205,751, filed 19 May 2000, entitled "Medical Image and Data Recordation System", all of which are herein incorporated by reference.

FIELD OF THE INVENTION

This invention relates to data storage and more particularly to determining end of incoming data stream in order to create jobs for recording and printing file information on a disc taken from the electronically stored information on the disc.

BACKGROUND OF THE INVENTION

In the past medical imaging such as x-rays were recorded on film and digital images were stored on digital film using film laser printers, which is expensive, bulky and difficult to store. Also, the original digital data might have to be modified so it can be printed using a laser printer since most printers can not handle high resolution or high quality digital data. Digital image storage allows storage and retrieval of original digital data on discs and transmittal of images over communications systems such as the internet.

There are printers combined with CD recording devices for printing on the disc that has just been recorded.

Medical imaging data is frequently manually stored on CD's and filed for later use in doctor's offices, hospitals, clinics and other medical facilities. The medical images may be generated by x-rays, cat scans, magnetic resonance images, sonograms or other image generating technologies.

Medical imaging data can be transmitted from one location to another over the internet or other communication system for recording the data. The filing and record keeping of the images thus received is a problem. It is a labor-intensive and error-prone task to gather information about each disc, write out labels and attach the labels to the discs, or write directly on the disc for storing and filing. It is very useful to have the information contained on a disc printed on the disc for reference and filing and for automatically creating a directory of the information stored on all the discs recorded in an office.

BRIEF SUMMARY OF THE INVENTION

The present invention automatically scans data received for storage on the disc and prints selected fields of information directly on the discs for ease of file management. The invention also constantly updates a database having a directory of all patient records and the discs the patient data is stored on. Although the invention is described in terms of storing medical imaging data any data imbedded with information useful for filing and label printing can be used with the invention.

The Medical Data Recording System hardware consists of three main components: a computer server; a CD autoloader with printer; and a piracy prevention device. The software components are: DICOM® communication software; FilmX™ software for storing software for viewing the images on the CDs, software for selecting image information to be copied to the CD and fields for printing on the discs; software for creating and updating a database of patient information and autoloader control software for the CDR and printer; and security device driver software.

The computer server communicates with other medical devices on the network using the DICOM® protocol. It receives medical images (patient studies) from other devices, processes the images and burns each patient's images on one or more CDRs along with medical image viewing software and other files as defined by the DICOM® protocol as well as files containing printed label definition and graphics files, files containing patient and study demographics, and necessary system files to make the CD autorun and autoload. Once a CDR has been burnt, information regarding the contents of the CDR and other graphics (company logo, legal notices, etc) is then printed directly on the CDR using the printer attached to the autoloader. Optionally, the system will create back up copies of the medical images it has received by burning them on CDR at configured days of the week and time. Each back up CDR will contain as many patients' images as possible to maximize disc space usage. Each backup disc is assigned a serial number which is printed on it. The patient and study demographics of the backed up data along with the corresponding backup disc serial number is stored in a database where they can queried.

Additional advantages and features of the invention will be set forth in part in the description which follows, and in part, will become apparent to those skilled in the art upon examination of the following or may be learned by practice of the invention.

OBJECTS OF THE INVENTION

It is an object of the invention to print information from selected fields of data saved on a disc onto the disc for visual recognition such that the discs can be properly stored in files.

It is an object of the invention to reduce clerical time and reduce errors by having discs printed with information fields from files stored on the discs.

It is an object of the invention to automatically load discs for information storage.

It is an object of the invention to automatically stop recording when the information stream has stopped and load a new disc for the next patient.

It is an object of the invention to print trademarks, service marks and logos on the discs.

It is an object of the invention to print selectable fields of information on the discs.

It is an object of the invention to back up files at specified time intervals.

It is an object of the invention to get as many images as possible onto one CDR.

It is an object of the invention to conveniently store medical image data on CD's rather than on film.

It is an object of the invention to be able to use a computer display to view medical images stored on CD's.

It is an object of the invention to preserve medical images for long periods of time.

It is an object of the invention to create patient files with directories and subdirectories from image data streams.

It is an object of the invention to divide data streams into separate files.

It is an object of the invention to automatically create and update file databases to locate patient information on the discs.

Other objects, advantages and novel features of the present invention will become apparent from the following detailed description of the invention when considered in conjunction with the accompanying drawing.

DETAILED DESCRIPTION

Figure 1:
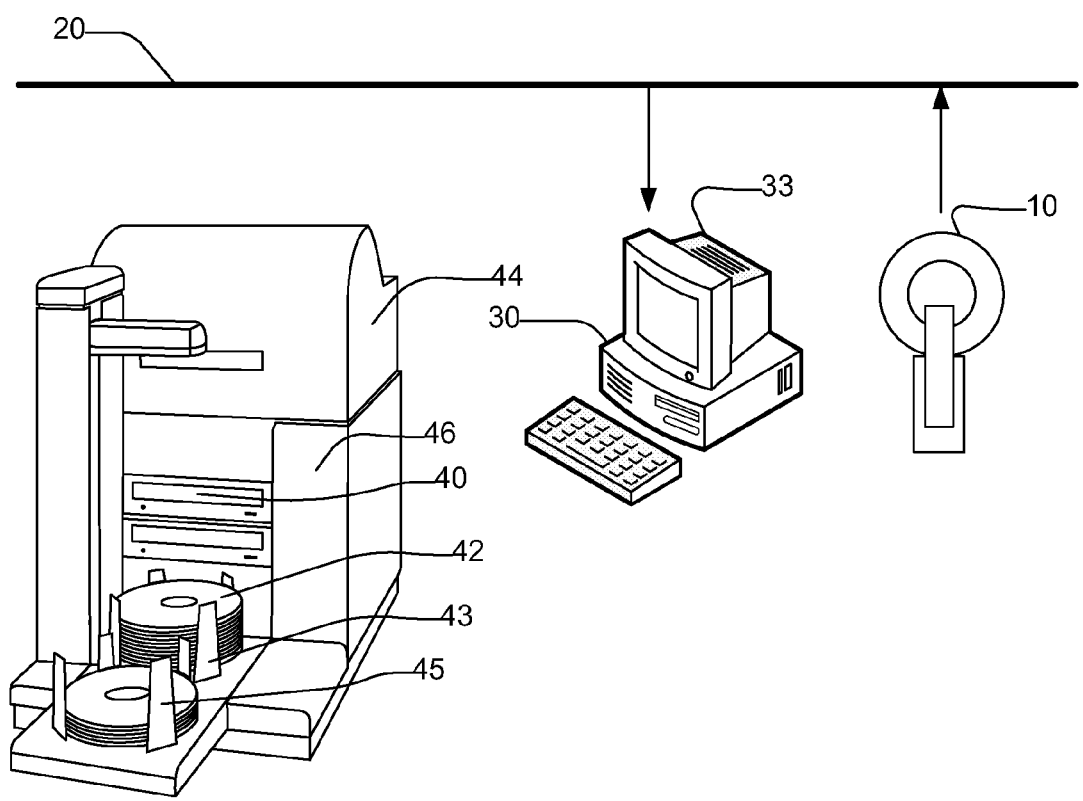
FIG. 1 shows a schematic of the system using the data recording system.
Figure 2:
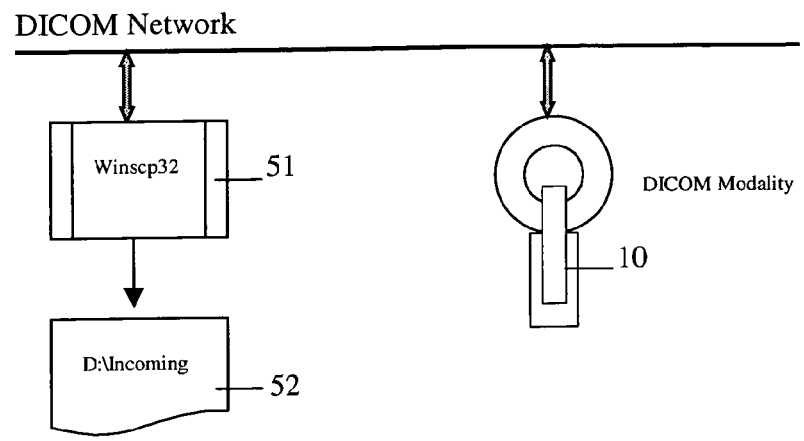
FIG. 2 shows a block diagram of the software steps used in the computer for receiving files from the network and storing them on the computer.
Figure 3:
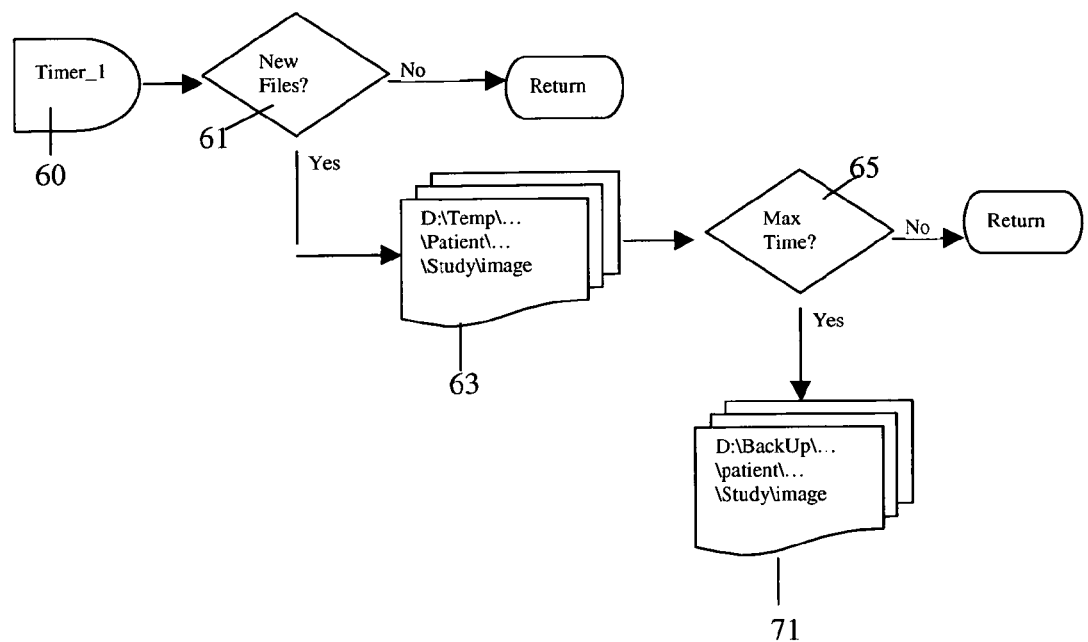
FIG. 3 shows the routine for determining the data for jobs from incoming files.
Figure 4:
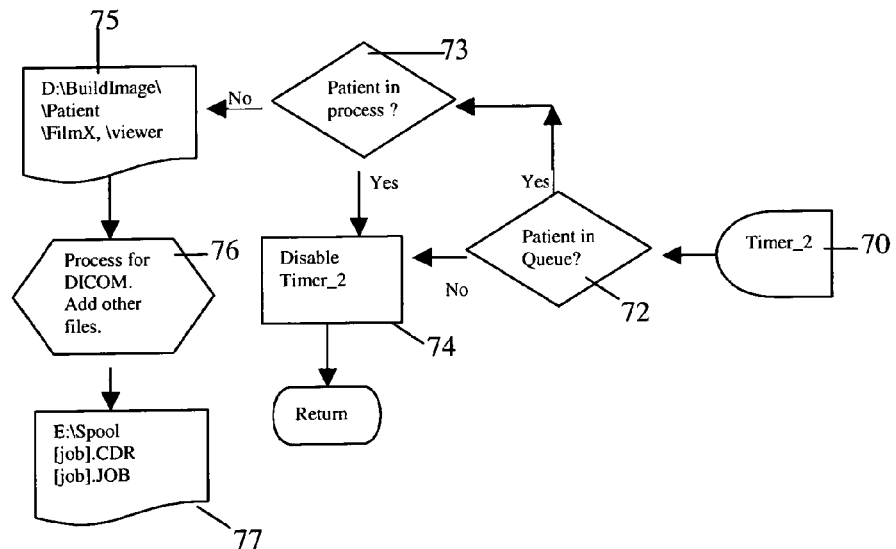
FIG. 4 shows the routine for processing jobs in queue.
Figure 5:
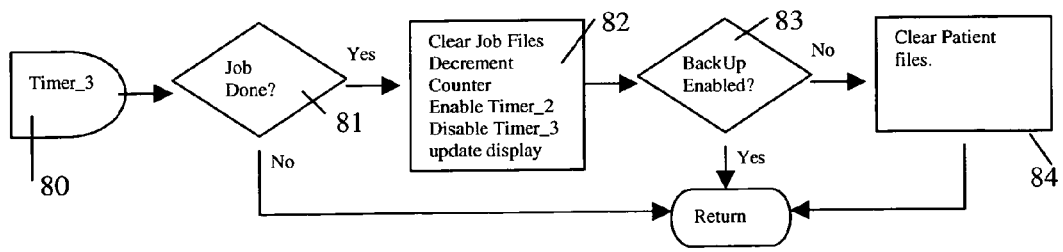
FIG. 5 shows the routine for checking for end of jobs.
Figure 6:
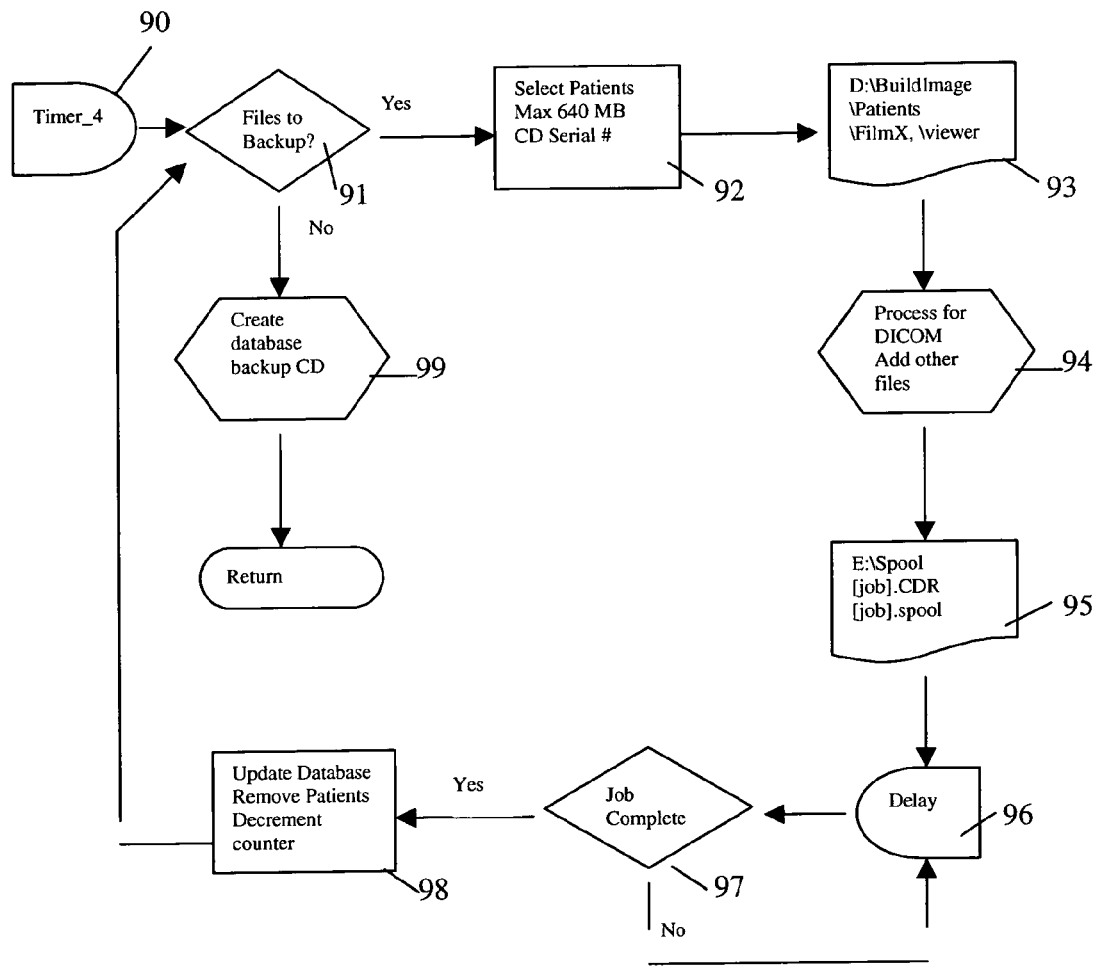
FIG. 6 shows the routine for the backup process.

FIG. 1 shows a schematic view of the invention. A medical imaging device 10 such as an x-ray, cat scan, magnetic resonance imaging, sonogram or other device which generates information for storage on a disc or generates images of a patient and either transmits it or stores it for later transmittal through a communication network 20 such as the internet to a computer 30. The computer 30 can be used to select information to be stored by the compact disc writer 40 on compact discs, CDs, 42 and can select what information is to be printed by printer 44 on discs 42. Although CDs 42 are shown, any recording medium may be used for storage of information. The blank compact discs 42 are stacked in an input CD stack 43 waiting to be recorded. The CD autoloader 46 selects CDs 42 from the top of the input CD stack 43 to be recorded on and places the CDs 42 into the recorder 40. When the CD 42 has information stored on it, it is moved by the CD autoloader 46 to the printer 44 where selected information and logos or other graphics are printed on the CD 42 so that the users have a written record on the disc of the information stored thereon and logos identifying the producer of the disc or other information. The CDs 42 are then removed from the printer 44 by CD autoloader 46 and placed in the CD output tray 45. The CDs 42 can then be placed in patient files.

The software for running the invention performs several tasks. There is security software communicating to an attached piracy prevention security device that keeps track of how many CDs are being recorded and what product option are active. There is software to run the autoloading functions of the CD autoloader 46 for recording and moving discs 42. The software also can be programmed to select the fields of information to be printed on the discs and for printing logos or other graphics or information on the discs. The software also copies instructions for operating the imaging onto the disc so that a computer without imaging software loaded in it can view the images on the discs.

Although many different software programs can be used to accomplish the goals set out above the following shows one method of securing image information for later viewing and recording it on discs with labels printed thereon. The software described herein is called FilmX™ software by the applicant.

FilmX™ software is used to receive data in the computer 30 from the communication network 20. The software incorporates DICOM® network connectivity software 51 such as WinSCP32.exe which is currently a standard digital imaging protocol used in the industry to receive the digital imaging data from the imaging device 10. The imaging data is received in the computer 30 by use of network connectivity software 51 using "winSCP32.exe" software available from ETIAM Corporation; Rennes, France. This program is a Storage Service Class Provider using the DICOM® protocol. The computer 30 receives DICOM® images that are sent to it and places them in the Incoming ("D:.backslash.Incoming") directory 52. The files are named: <Storage SOP Class>.<SOP Instance UID>.dcm where <Storage SOP Class> is the SOP class of the image and <SOP Instance UID> is the image UID (Unique Identifier).

There are multiple timers defined with in FilmX.exe. Timer.sub.--1 60 is responsible for checking for incoming new files 61 in Incoming Directory 52. If new files are received they are stored as a separate file in a temporary directory Temp Directory 63. Timer.sub.--1 60 is programmed to check if an end-of-patient-data timeout (MaxTime) 65 has occurred. The value for Timer.sub.--1 60 is defined in the FilmX.ini file and is hence user configurable. Default time for Timer.sub.--1 60 is 1 (one) second. Max Time 65 is also user configurable via FilmX.ini and is set to 30 seconds for default. The system will not allow that time to be set less than 10 seconds. Once the Timer.sub.--1 60 goes off, two routines are called:

DcmBTreeParseInputDirectory dcmBTreeMakePatientDataAvailable

The first routine parses any DICOM Part 10 file found in Incoming Directory 52. If any new files 61 are available, they are transferred to the Temp Directory (d:.backslash.Temp) 63. For each different patient, a subdirectory is created under the Temp Directory 63, and for each study of this patient, a subdirectory is created under the patient directory.

Patient differentiation is based on Patient Identification which consists of the concatenation of information found in DICOM® datasets: PatientsID '_' PatientsName, without any ' ', any white character or any character that may lead to an invalid Windows directory name, all characters are uppercase and enclosing blanks are removed. Patient Directory name underneath Temp Directory 63 is the Patient Identification described above.

Study identification is based on the StudyInstanceUID. Study Directory name beneath the Patient Directory is the study identification referenced above.

Filenames are the original filenames found in Incoming Directory 52. This allows the system to override an image if it is sent twice.

An additional text file is created in each Patient Directory. This file has a fixed name (timestamp.bsy) and contains the date and time of the last image insertion in the Patient hierarchy. The following information is also written in this file:

PatientsName

PatientsSex

PatientsBirthDate

An additional text file is created in each Study Directory. This file has a fixed name (study.dsc) and contains the information extracted from the last image of the study inserted in the Study Directory. This information is as follows:

StudyDate

StudyTime

StudyID

StudyDescription

RefferringPhysiciansName

Accession Number.

Once DcmBTreeParseInputDirectory has returned, any new patients are added to the Incoming Patient Queue and displayed on the screen as such. The combination of patient "[id]_[name]" is now the internal job name used for tracking the job.

Then dcmBTreeMakePatientDataAvailable is called to check in Temp Directory 63 if any patient subdirectories have not been modified (some images added) since MaxTime 65 seconds ago. The number of unmodified directories since MaxTime 65 seconds is returned. If no new files 61 have arrived for a patient, the timestamp file (timestamp.bsy) for the patient will be renamed to a fixed filename (timestamp.rdy).

Once the function returns a positive number, we browse for Patient Directories in the Temp Directory 63 containing "timestamp.rdy" file. The entire patient hierarchy is then moved to the Backup Directory 71 (D:.backslash.Backup). The Job is then removed from the Incoming Patient Queue and added to the Pending Patient Queue and displayed as such. If inactive, Timer.sub.--2 70 is activated to start processing the pending job(s).

Timer.sub.--2 70 is responsible for moving jobs pending in Queue to be processed. Once it goes off, the system is checked for any patient in queue 72, if none are present, Timer.sub.--2 70 is disabled in step 74. If there are pending jobs in Pending Patient Queue, the system is checked for patient in process 73 (being recorded or printed). If there is one, Timer.sub.--2 70 is disabled and it returns. If there are no patients in process 73, the next job in Pending Patient Queue, is processed. The patient directory hierarchy in Backup Directory 71 is moved to the Build Image Directory 75 (D:.backslash.Build Image) to get ready to burn on CDR(s). The Build Image Directory 75 also contains a Viewer Directory (".backslash.Viewer) where the viewing software resides. There is also a FilmX Directory ("FilmX") in the Build Image Directory 75 which contains the Patient information file ("Patient.txt") and the Xlabel Directory (".backslash.Xlabel") where the CD printing label definitions and graphics files reside. Since DICOM® Exchange standards only allow for eight character file names, the Patient, and Study directories as well as image file names are converted to eight character format in processing step 76. The Patient Directory name is changed to "PT000000" for the first patient. In case of back up CD, Patient Directories are then sequentially named "PT000001" and so on. The Study Directory(ies) are named starting with "ST000000" and increase sequentially if there is more then one study for the patient. The image files are then named starting with "IM000000" and so on. On the Build Image Directory 75 there is also an "autorun" file which is recognized by the Windows operating system and executed when a disc is inserted in a computer. The "autorun" file contains instructions to start the viewer in an "autoload" fashion causing it to immediately load and display the first Patient's first Study. Finally, according to DICOM® Exchange standard, a "DICOMDIR" file is generated in step 76 in the Build Image Directory 75.

Once the Build Image Directory 75 is complete, it represents what should be put on the final CDR with Build Image Directory 75 as the root of the CD. The computer program "Premaster.exe" is then called to create a CD image of the contents of the Build Image Directory 75. This program is part of the BuzzSaw® software package produced by ISO Media of Seattle, Wash. The result is a "[job].CDR" file which is the image of the final CDR. It is located in the Spool Directory 77 (E:.backslash.Spool). A "[job]job" file containing the job control information for the autoloader control software (Buzzsaw®) is created in the Spool Directory 77. The Job file specifies the name of the CDR file, the input file for the print label fields, the number of CDRs to be made, the test flag, and other fields as required by the Buzzsaw® software. Once the CD image files is generated in the Spool Directory 77, the Build Image Directory 75 is then cleared of the patient directory and other created files. Once created, the job file is recognized by the Buzzsaw® software and processed.

Buzzsaw® instructs the autoloader 46 to pick up a new CDR 42, put it in the CDR drive 40. Once there, Buzzsaw® will proceed to record the contents of [job].CDR" file on the CDR 42 in the drive 40. In multi-copy, multi-drive situations, Buzzsaw® will place new CDRs 42 in other drives 40 as well and record them simultaneously. Once the recording is finished, Buzzsaw® instructs the autoloader 46 to place the recorded CDR 42 in the Disc Printer 44. It will then execute the printing software to print the label containing the input fields on the CDR.

The label printing software and printer driver are supplied by Primera Technologies; Plymouth, Minn., a disc printer manufacturer. The label definitions allow for input fields to be merged into the label via a merge file in Build Image Directory 75. The patient.txt file in the Build Image directory 75 is that merge file.

Once printed, the CDR 42 is then placed in the output bin 45 by the autoloader 46. If there are multiple copies, the other CDRs 42 are then printed by the Disc Printer 44 and put on the output bin 45 as well by the autoloader 46. Buzzsaw® then updates the status line at the bottom of the "[job].JOB" file contained in the Spool Directory 77 to indicate the job is completed.

Timer.sub.--3 80 is responsible for checking the end of the job. Once Timer.sub.--3 80 goes off, the system checks for job done 81. If so, the job is moved from the Patients in Process to Patients completed and display is updated in step 82 where Timer.sub.--3 80 is cleared, and Timer.sub.--2 70 is enabled. If Backup Enabled 83 is false, the patient directory is deleted from Backup Directory 71. Otherwise, it will be kept there to be used during the backup.

Timer.sub.--4 90 starts the backup process. It is programmed to go off at the configured time on the configured day(s) of the week. The program then checks if there are any files to backup 91. This is also a check for the end of back up process. If finished (or nothing left to back up), a CDR 42 containing only the latest database files is generated 99. This is the backup disc for the database files. If there are files to backup 91, in Select Patients step 92 enough patients are selected to fill a 650 MB CD (if there are enough) minus approximately 10 MB which is used for storing system, label, and viewer files. A Backup CD unique serial number is also generated in Select Patients step 92. The patient directories are then moved from Backup Directory 71 to Build Image Directory 75. The same processing as for a patient CD, as described in steps 75-77 above then occur steps 93-95. Once a backup job is created, the software then goes through a timed delay 96 waiting for the job to finish by checking for job complete 97. Once done, the database is updated with the patient and study information of all the patients on that CD and the CD unique serial number in Update Database step 98. The process starts anew by checking to see if there are any more files to back up 91.

A simple query screen allows for querying the backup database using patient name, patient id, or study date thus allowing the user to find which CD a patient information is stored on.

The piracy protection device is attached to the parallel port. It is initialized with the number of CDRs 42 purchased, and with patient and/or backup options. FilmX™ will create patient CDs if that option is enabled; back up CDs if that option is enabled; and ii both if both options are present. Once a job has been successfully completed, the number of CDs created by it are deducted from the counter in the piracy protection device. If at Zero, the system halts operation until a new code for additional CDs has been entered. Patient and/or backup options can be enabled by operator entering a code provided by Soma Corporation.

Even though the invention has been described herein using CDRs, other printable recording medium, including but not limited to CDR, CDRW, DVD-R, DVD-RW, DVDRAM; can be used.

Obviously, many modifications and variations of the present invention are possible in light of the above teachings. It is therefore to be understood that, within the scope of the appended claims, the invention may be practiced otherwise than as specifically described.

What is claimed is:

1. A non-transitory machine-readable medium providing instructions that, when executed by a machine, cause the machine to perform operations comprising:
    receiving medical data information in DICOM format through a software module and extracting patient identification information and study information from the received medical data information, the medical data further comprising one or more files;
    storing the extracted patient identification information and extracted study information, the stored extracted study information and patient identification information coming from the one or more files;
    storing DICOM image information coming from the one or more files;
    determining an end of the received medical data information through the software module for each patient;
    creating a job containing the medical data for a patient; and
    providing print information for a record and print control software, the print information having selected fields obtained from an automatic scan of the stored extracted patient identification information and the stored extracted study information;
    submitting the job to the record and print control software;
    recording said DICOM image information from the one or more files on a recording media;
    recording other files as defined by DICOM on the recording media;
    automatically printing the selected fields of the automatic scan of the stored extracted patient identification information and the stored extracted study information on the recording media to label the recording media.

2. The non-transitory machine-readable medium of claim 1 providing instructions that, when executed by a machine, cause the machine to perform operations comprising:
    associating a serial numbering device for associating a serial number with the recording media; and
    storing the medical data information associated with the serial number and the associated recording media in a searchable format.

3. The non-transitory machine-readable medium of claim 1 wherein the instructions for receiving medical information that, when executed by a machine, further cause the machine to perform operations comprising:
    receiving medical information in a form of a DICOM file for a plurality of patients, the medical information including images, patient identification information and study information;
    sorting the medical information based on patient identity information;
    associating at least one DICOM file associated with medical information on the recording media; and
    automatically labeling the recording media, the label including at least a portion of selected medical information, the portion of the selected medical information associated with a content of the at least one DICOM file stored on the recording media.

4. The non-transitory machine-readable medium of claim 1 further providing instructions that, when executed by a machine, cause the machine to perform operations comprising storing the patient identification information on said recording media at another memory location.

5. The non-transitory machine-readable medium of claim 4 providing instructions that, when executed by a machine, cause the machine to perform operations wherein storing the patient identification information on said recording media at another memory location is part of backing up the medical data information.

6. The non-transitory machine-readable medium of claim 1 providing instructions that, when executed by a machine, cause the machine to perform operations comprising;
    storing the patient identification information on said recording media at another memory location; and
    associating a unique identifier with the recording media and with the patient identification information at another memory location.

7. The non-transitory machine-readable medium of claim 1 further comprising recording a medical data viewing software on the recording media.

8. The non-transitory machine-readable medium of claim 1 providing instructions that, when executed by a machine, cause the machine to perform operations wherein the recording media is loaded, and moved automatically.

9. The non-transitory machine-readable medium of claim 1 providing instructions that, when executed by a machine, cause the machine to perform operations wherein the label for the recording media includes selected logos, trademarks or images.

10. The non-transitory machine-readable medium of claim 1 providing instructions that, when executed by a machine, cause the machine to perform operations wherein the receiving medical data information includes receiving a plurality of files at different times.

11. The non-transitory machine-readable medium of claim 1 providing instructions that, when executed by a machine, cause the machine to perform operations wherein determining the end of the received medical data information comprises utilizing a time out period.

12. The non-transitory machine-readable medium of claim 1 providing instructions that, when executed by a machine, cause the machine to perform operations wherein the receiving medical data information includes receiving a plurality of patient files for different patients at different times.

13. The non-transitory machine-readable medium of claim 1 providing instructions that, when executed by a machine, cause the machine to perform operations comprising
    updating a database having a directory of patient records and the recording media on which the medical data is stored.

14. The non-transitory machine-readable medium of claim 1 further providing instructions that, when executed by a machine, cause the machine to perform operations comprising storing the study information on said recording media at another memory location.

15. The non-transitory machine-readable medium of claim 1 further providing instructions that, when executed by a machine, cause the machine to perform operations comprising storing the DICOM image information on said recording media at another memory location.

16. The non-transitory machine-readable medium of claim 1 providing instructions that, when executed by a machine, cause the machine to perform operations comprising;

storing the study information on said recording media at another memory location; and associating a unique identifier with the recording media and with the study information at another memory location.

17. The non-transitory machine-readable medium of claim 1 providing instructions that, when executed by a machine, cause the machine to perform operations comprising;

storing the DICOM image information on said recording media at another memory location; and associating a unique identifier with the recording media and with the DICOM image information at another memory location.

18. A medical data recording method comprising:

receiving medical data information in DICOM format through a software module and extracting patient identification information and study information from the received medical data information, the medical data further comprising one or more files;

storing the extracted patient identification information and extracted study information, the stored extracted study information and patient identification information coming from the one or more files;

storing DICOM image information coming from the one or more files;

determining an end of the received medical data information through the software module for each patient;

creating a job containing the medical data for a patient; and providing print information for a record and print control software, the print information having selected fields obtained from an automatic scan of the stored extracted patient identification information and the stored extracted study information;

submitting the job to the record and print control software;

recording said DICOM image information from the one or more files on a recording media;

recording other files as defined by DICOM on the recording media; and automatically printing the selected fields of the automatic scan of the stored extracted patient identification information and the stored extracted study information on the recording media to label the recording media.

19. The medical data recording method of claim 18 further comprising:

associating a serial numbering device for associating a serial number with the recording media; and storing the medical data information associated with the serial number and the associated recording media in a searchable format.

20. The medical data recording method of claim 18 further comprising:

receiving medical information in a form of a DICOM file for a plurality of patients, the medical information including images, patient identification information and study information;

sorting the medical information based on patient identity information;

associating at least one DICOM file associated with medical information on the recording media; and automatically labeling the recording media, the label including at least a portion of selected medical information, the portion of the selected medical information associated with a content of the at least one DICOM file stored on the recording media.

21. The medical data recording method of claim 18 further comprising storing the DICOM image information on said recording media at another memory location.

22. The medical data recording method of claim 18 further comprising;

storing the DICOM image information on said recording media at another memory location; and associating a unique identifier with the recording media and with the DICOM image information stored at another memory location.

23. The medical data recording method of claim 18 wherein storing the DICOM image information on said recording media at another memory location is part of backing up the medical data information.

24. The medical data recording method of claim 18 further includes recording a medical data viewing software on the recording media.

25. The medical data recording method of claim 18 wherein the recording media is loaded, and moved automatically.

26. The medical data recording method of claim 18 wherein the recording media is recorded and labeled at substantially one position.

27. The medical data recording method of claim 18 wherein the label for the recording media includes selected logos, trademarks or images.

28. The medical data recording method of claim 18 wherein the receiving medical data information includes receiving a plurality of files at different times.

29. The medical data recording method of claim 18 wherein determining the end of the received medical data information comprises utilizing a time out period.

30. The medical data recording method of claim 18 wherein the receiving medical data information includes receiving a plurality of patient files for different patients at different times.

31. The medical data recording method of claim 18 further comprising updating a database having a directory of patient records and the recording media on which the medical data is stored.

32. A medical data recording system comprising:

a receiver module for receiving medical data information in DICOM format through a software module and extracting patient identification information and study information from the received medical data information, the medical data further comprising one or more files;

memory for storing the extracted patient identification information and extracted study information, the stored extracted study information and patient identification information coming from the one or more files;

said memory also storing DICOM image information coming from the one or more files;

a determiner for determining an end of the received medical data information through the software module for each patient;

a job creation module for creating a job containing the medical data for a patient; and a print information module for providing print information for a record and print control software, the print information having selected fields obtained from an automatic scan of the stored extracted patient identification information and the stored extracted study information;

the print information module submitting the job to the record and print control software;

a burner for recording said DICOM image information from the one or more files on a recording media;

the burner also recording other files as defined by DICOM on the recording media; and a printer module for automatically printing the selected fields of the automatic scan of the stored extracted patient identification information and the stored extracted study information on the recording media to label the recording media.

33. The medical data recording system of claim 32 further comprising:
an association module for associating a serial numbering device for associating a serial number with the recording media, said memory storing the medical data information associated with the serial number and the associated recording media in a searchable format.

34. The medical data recording system of claim 33
wherein the receiver module receives the medical data information in a form of a DICOM file for a plurality of patients, the medical data information including images, patient identification information and study information, and
sorts the medical data information based on patient identity information;
the association module associates at least one DICOM file with medical information on the recording media; and
the printer module automatically labels the recording media, the label including at least a portion of selected medical information, the portion of the selected medical information associated with a content of the at least one DICOM file stored on the recording media.

35. The medical data recording system of claim 32 further comprising another memory location for storing the DICOM image information on said recording media to back up the medical data information.

36. The medical data recording system of claim 32 wherein the burner records a medical data viewing software on the recording media.

37. The medical data recording system of claim 32 wherein the recording media is loaded, and moved automatically.

38. The medical data recording system of claim 32 wherein the recording media is recorded and labeled at substantially one position.

39. The medical data recording system of claim 32 further comprising an update module for updating a database having a directory of patient records and the recording media on which the medical data is stored.

40. A non-transitory machine-readable medium providing instructions that, when executed by a machine, cause the machine to perform operations comprising:
receiving medical data information in DICOM format through a software module and extracting patient identification information and study information from the received medical data information, the medical data further comprising one or more files;
storing the extracted patient identification information and extracted study information, the stored extracted study information and patient identification information coming from the one or more files;
storing DICOM image information coming from the one or more files;
determining an end of the received medical data information through the software module for each patient, the end determination utilizing a time out period;
creating a job containing the medical data for a patient; and
providing print information for a record and print control software, the print information having selected fields obtained from an automatic scan of the stored extracted patient identification information and the stored extracted study information;
submitting the job to the record and print control software;
recording said DICOM image information from the one or more files on a recording media;
recording other files as defined by DICOM on the recording media; and
printing the selected fields of the automatic scan of the stored extracted patient identification information and the stored extracted study information on the recording media to label the recording media.

41. A medical data recording method comprising:
receiving medical data information in DICOM format through a software module and extracting patient identification information and study information from the received medical data information, the medical data further comprising one or more files;
storing the extracted patient identification information and extracted study information, the stored extracted study information and patient identification information coming from the one or more files;
storing DICOM image information coming from the one or more files;
determining an end of the received medical data information through the software module for each patient;
creating a job containing the medical data for a patient; and
providing print information for a record and print control software, the print information having selected fields obtained from a scan of the stored extracted patient identification information and the stored extracted study information;
submitting the job to the record and print control software;
recording said DICOM image information from the one or more files on a recording media;
recording other files as defined by DICOM on the recording media; and
printing the selected fields from the scan of the stored extracted patient identification information and the stored extracted study information on the recording media to label the recording media.

42. A non-transitory machine-readable medium providing instructions that, when executed by a machine, cause the machine to perform operations comprising:
receiving medical data information in DICOM format through a software module and extracting patient identification information and study information from the received medical data information, the medical data further comprising one or more files;
storing the extracted patient identification information and extracted study information, the stored extracted study information and patient identification information coming from the one or more files;
storing DICOM image information coming from the one or more files;
determining an end of the received medical data information through the software module for each patient;
creating a job containing the medical data for a patient; and
providing print information for a record and print control software, the print information having selected fields obtained from a scan of the stored extracted patient identification information and the stored extracted study information;
submitting the job to the record and print control software;
recording said DICOM image information from the one or more files on a recording media;
recording other files as defined by DICOM on the recording media; and
printing the selected fields from the scan of the stored extracted patient identification information and the stored extracted study information on the recording media to label the recording media.

* * * * *